(12) United States Patent
Bailey et al.

(10) Patent No.: US 7,039,530 B2
(45) Date of Patent: May 2, 2006

(54) FLUID MEASUREMENT

(75) Inventors: John H. Bailey, Shelton, CT (US);
Jeffrey C. Adams, Westerly, RI (US);
Rudolf Kren, Niantic, CT (US);
Armand E. Halter, Gales Ferry, CT (US)

(73) Assignee: Ashcroft Inc., Stratford, CT (US)

( * ) Notice: Subject to any disclaimer, the term of this patent is extended or adjusted under 35 U.S.C. 154(b) by 50 days.

(21) Appl. No.: 10/750,103

(22) Filed: Dec. 29, 2003

(65) Prior Publication Data
US 2005/0149277 A1 Jul. 7, 2005

(51) Int. Cl.
*G01L 7/00* (2006.01)
*G01F 17/00* (2006.01)

(52) U.S. Cl. .............. 702/50; 73/1.83; 73/290 V; 73/861.18; 73/861.29; 141/95; 702/55; 702/56

(58) Field of Classification Search ............ 702/12–13, 702/42, 45, 50–54, 55–56, 100; 73/1.83, 73/290 V, 861.18, 861.356, 589, 861.29; 141/95
See application file for complete search history.

(56) References Cited

U.S. PATENT DOCUMENTS

| | | | | |
|---|---|---|---|---|
| 3,224,246 A | * | 12/1965 | Schloss et al. | ............ 73/1.83 |
| 3,958,458 A | * | 5/1976 | Foreman et al. | ......... 73/861.18 |
| 4,320,659 A | | 3/1982 | Lynnworth et al. | ........... 73/589 |
| 4,487,065 A | | 12/1984 | Carlin et al. | ............. 73/290 V |
| 4,730,650 A | * | 3/1988 | Ziegler et al. | ................ 141/95 |
| 5,440,937 A | * | 8/1995 | Lynnworth et al. | ...... 73/861.29 |
| 6,053,041 A | * | 4/2000 | Sinha | ...................... 73/290 V |
| 6,192,751 B1 | * | 2/2001 | Stein et al. | ............... 73/290 V |
| 6,412,354 B1 | * | 7/2002 | Birchak et al. | ........ 73/861.356 |
| 6,424,922 B1 | | 7/2002 | Bray | ........................... 702/42 |
| 6,477,473 B1 | | 11/2002 | Bray | .......................... 702/42 |
| 6,523,418 B1 | | 2/2003 | Bray | ........................... 73/801 |
| 6,631,639 B1 | | 10/2003 | Dam et al. | ............... 73/290 V |

FOREIGN PATENT DOCUMENTS

| | | |
|---|---|---|
| EP | 0 621 462 A2 | 10/1994 |
| EP | 1 059 516 A1 | 12/2000 |

OTHER PUBLICATIONS

"Modern Ultrasonic Transducers", Ultran, 1999.*
Basic Principles of Ultrasonic Testing, http://www.ndt-ed.org/EducationResources/CommunityCollege/Ultrasonics/Introduction, Oct. 8, 2003, 3 pages.
Wave Propagation, http://www.ndt-ed.org/EducationResources/CommunityCollege/Ultrasonics/Physics, Oct. 8, 2003, 2 pages.
Modes of Sound Wave Propagation, http://www.ndt-ed.org/EducationResources/CommunityCollege/Ultrasonics/Physics, Oct. 8, 2003, 2 pages.
Properties of Acoustic Plane Wave, http://www.ndt-ed.org/EducationResources/CommunityCollege/Ultrasonics/Introduction, Oct. 8, 2003, 2 pages.

(Continued)

*Primary Examiner*—Bryan Bui
*Assistant Examiner*—John Le
(74) *Attorney, Agent, or Firm*—Fish & Richardson P.C.

(57) ABSTRACT

Techniques for fluid measurement include the ability to introduce a vibration to a container wall and to detect the vibration after the vibration has propagated at least partially around the container wall. Based on the detection of the vibration, the techniques also include the ability to determine a fluid state.

8 Claims, 2 Drawing Sheets

OTHER PUBLICATIONS

Wavelength and Defect Detection, http://www.ndt-ed.org/EducationResources/CommunityCollege/Ultrasonics/Physics, Oct. 8, 2003, 2 pages.

Sound Propagation in Elastic Materials, http://www.ndt-ed.org/EducationResources/CommunityCollege/Ultrasonics/Physics, Oct. 8, 2003, 3 pages.

Attenuation of Sound Waves, http://www.ndt-ed.org/EducationResources/CommunityCollege/Ultrasonics/Physics, Oct. 8, 2003, 2 pages.

Acoustic Impedance, http://www.ndt-ed.org/EducationResources/CommunityCollege/Ultrasonics/Physics, Oct. 8, 2003, 2 pages.

Reflection and Transmission Coefficients (Pressure), http://www.ndt-ed.org/EducationResources/CommunityCollege/Ultrasonics/Physics, Oct. 8, 2003, 2 pages.

Refraction and Snell's Law, http://www.ndt-ed.org/EducationResources/CommunityCollege/Ultrasonics/Physics, Oct. 8, 2003, 3 pages.

Mode Conversion, http://www.ndt-ed.org/EducationResources/CommunityCollege/Ultrasonics/Physics, Oct. 8, 2003, 3 pages.

Katronic Technologies Ltd. Manual, Sonometer 11, May 1997, 2 pages.

KATRONIC Clamp-on Ultrasonic Flowmeters and other Non-invasive Process Measure . . . , Oct. 7, 2003, 2 pages.

KATRONIC Non-invasive Ultrasonic Instrumentation for Flow, Level, Density and Conc . . . , Oct. 7, 2003, 2 pages.

KATRONIC Measuring Principle Non-invasive Level Measurement & Control, Oct. 7, 2003, 2 pages.

KATRONIC Non-invasive Continuous Level Measurement, Oct. 7, 2003, 2 pages.

Katronic Technologies Ltd. Manual, Sonometer 30, Jun. 1998, 2 pages.

MTS Liquid Level Sensors, http://www.technology.mtslevelsensors.com, Oct. 10, 2003, 1 page, 2 pages.

MTS Commercial Level Sensors, http://www.technology.mtslevelsensors.com, Oct. 10, 2003, 2 pages.

MTS Liquid Level Sensors, http://www.technology.mtslevelsensors.com/namedPageViewer.php?keyword=sef, Oct. 10, 2003, 2 pages.

Current directions of Ultrasonic Stress Measurement Techniques, Don E. Bray, Ph.D., http://www.ndt.net/article/wcndt00/papers/idn647/idn647.htm, Oct. 15, 2003, 8 pages.

Ultrasonic Stress Measurement With the $L_{CR}$ Technique, Don E. Bray, http://brayengr.com/lcrproc2.html, Oct. 15, 2003, 14 pages.

PCT International Search Report, PCT/US2004/041317, Apr. 19, 2005, pp. 1-4.

Paul Panetta, George Alers, Bob Francini, Aaron Diaz, Ken Johnson, Marino Morra, and Dan Kerr, "Ultrasonic Measurements of Plastic Strain in Pipelines," Sep. 26, 2002, Pacific Northwest National Laboratory, Richland, WA, pp. 1-25.

* cited by examiner

FLUID MEASUREMENT

TECHNICAL FIELD

The following description relates generally to measurement techniques, and, more particularly, to techniques for measuring fluids.

BACKGROUND

Fluid measurement devices are widely utilized in a myriad of different environments for commercial and industrial applications. Fluid measurement devices may, for example, be used to measure the temperature, the pressure, and/or the amount of a fluid. Fluid measurement devices may also be used to measure other appropriate factors regarding a fluid.

A common measurement for fluid measurement devices that measure the amount of a fluid is measuring the level of a fluid in a container, such as a rail car. With such a measurement, an operator may understand how full, or empty, a container is. Examples of devices for measuring fluid level in a container include mechanical float arms, radar, and pressure transducers. Another example is a sensor that measures the strain of a support of a tank. Based on the strain of the support, the mass of the fluid may be determined, along with the volume and fluid level.

SUMMARY

Techniques for measuring a fluid in a container include the ability to analyze a vibration after it has propagated at least partially around a container wall. The vibration, which may, for example, propagate as a longitudinal wave, a shear wave, or both, may be introduced to the container wall, allowed to propagate a certain distance in the wall, detected, and analyzed. Based on the analysis of the vibration, a state of the fluid may be determined. A state of a fluid may, for example, include the fluid's mass, volume, or level.

In one general aspect, a system for measuring fluid in a container includes one or more transducers and a computer. The one or more transducers are operable to introduce a vibration to a container wall, to detect an introduced vibration that has propagated at least partially around a container wall, and to generate a signal representative of a detected vibration. The computer is operable to determine a state of a fluid in a container based on a signal representing an introduced vibration that has propagated at least partially around a container wall. The fluid state may, for example, be a level of a fluid.

The one or more transducers may, for example, include a first transducer. The first transducer may be operable to introduce a vibration to a container wall. The first transducer may, for instance, be an air transducer and may generate a vibration between approximately 30 kHz and 150 kHz. The one or more transducers may be adapted to couple to the exterior of a container.

The computer may determine a fluid state in a container in a variety of manners. For example, the computer may determine a fluid state in a container based on the time for an introduced vibration to propagate at least partially around a container wall to a detecting transducer. As another example, the computer may determine a fluid state in a container based on the amplitude of an introduced vibration at detection. As a further example, the computer may determine a fluid state in a container based on the time for an introduced vibration to propagate at least partially around a container wall to a detecting transducer and the amplitude of the introduced vibration at detection.

The computer may be further operable to control an introducing transducer. If operable to control an introducing transducer, the computer may control the amplitude and frequency of vibrations introduced by the introducing transducer. The computer may also determine a second fluid state.

In certain implementations, the system may also include a wireless communication device. The wireless communication device may be operable to send a wireless signal representing a generated signal to the computer.

In another general aspect, a method for measuring fluid in a container includes introducing a vibration to a container wall and detecting the vibration in the container wall after the vibration has propagated at least partially around the container wall. The method also includes determining a state of a fluid in the container based on the detection of the vibration.

Determining a fluid state based on the detection of the vibration may be accomplished in a variety of manners. For example, a fluid state may be determined by determining the time for the vibration to propagate at least partially around the container wall to a detection point. As another example, a fluid state may be determined by determining the amplitude of the vibration at detection. As a further example, a fluid state may be determined by determining the time for the vibration to propagate at least partially around the container wall to a detection point and determining the amplitude of the vibration at detection.

The method may also include controlling the introduction of the vibration. The method may additionally include sending a wireless signal representing the detected vibration.

In certain general aspects, a system for measuring fluid in a container includes means for introducing a vibration to a container wall and means for detecting an introduced vibration that has propagated at least partially around a container wall and for generating a signal representing a vibration at detection. The system also includes means for determining a state of a fluid in a container based on a signal representing an introduced vibration that has propagated at least partially around a container wall.

Determining a fluid state may be accomplished in a variety of manners. For example, a fluid state may be determined by determining the time for an introduced vibration to propagate at least partially around a container wall to the detection means. As another example, a fluid state may be determined by determining the amplitude of an introduced vibration at detection. As a further example, a fluid state may be determined by determining the time for an introduced vibration to propagate at least partially around a container wall to the detection means and determining the amplitude of the introduced vibration at detection. The introducing means and the detecting means may be adapted to couple to the exterior of a container.

In certain implementations, the determining means also controls the introducing means. The system may additionally include means for sending a wireless signal representing the generated signal to the determining means.

In another general aspect, a method for measuring fluid in a container includes receiving a signal representing a vibration detected after being introduced to and propagating at least partially around a container wall and determining a state of a fluid based on the signal.

Determining a fluid state based on the signal may be accomplished in a variety of manners. For example, a fluid state may be determined by determining the time for a represented vibration to propagate at least partially around a container wall to a detection point. As another example, a fluid state may be determined by determining the amplitude of a represented vibration at detection. As an additional example, a fluid state may be determined by determining the time for a represented vibration to propagate at least partially around a container wall to a detection point and determining the amplitude of the represented vibration at detection.

The method may also include controlling the introduction of the represented vibration. Additionally, receiving a signal may include receiving a wireless signal representing the signal.

In yet another general aspect, a system for measuring fluid in a container includes a computer operable to determine whether a signal representing a vibration detected after being introduced to and propagating at least partially around a container wall has been received and to determine a state of a fluid based on the signal.

Determining a fluid state based on the signal may be accomplished in a variety of manners. For example, a fluid state may be determined by determining the time for a represented vibration to propagate at least partially around a container wall to a detection point. As another example, a fluid state may be determined by determining the amplitude of a represented vibration at detection. As an additional example, a fluid state may be determined by determining the time for a represented vibration to propagate at least partially around a container wall to a detection point and determining the amplitude of the represented vibration at detection. The computer may also be operable to control the introduction of a vibration.

The system may also include a wireless communication device. The wireless communication device may be operable to send a wireless signal representing the signal.

In another general aspect, an article including a machine-readable medium storing instructions operable to cause one or more machines to perform operations is provided. The operations include determining whether a signal representing a vibration detected after being introduced to and propagating at least partially around a container wall has been received and determining a state of a fluid based on the signal.

Determining a fluid state based on the signal may be accomplished in a variety of manners. For example, a fluid state may be determined by determining the time for a represented vibration to propagate at least partially around a container wall to a detection point. As another example, a fluid state may be determined by determining the amplitude of a represented vibration at detection. As a further example, a fluid state may be determined by determining the time for a represented vibration to propagate at least partially around a container wall to a detection point and determining the amplitude of the represented vibration at detection.

In certain implementations, the instructions are further operable to cause one or more machines to perform operations including controlling the introduction of a vibration. The instructions may also be operable to cause one or more machines to perform operations including determining whether a wireless signal representing the signal has been received.

In particular general aspects, a system for measuring fluid in a container includes a container, a first transducer, a second transducer, a wireless communication device, a second wireless communication device, and a computer. The container is operable to hold a fluid and includes a wall having an inner surface and an exterior surface. The first transducer is coupled to the exterior surface of the container wall near the top of the container, and is operable to introduce a vibration to the container wall. The second transducer is also coupled to the exterior surface of the container wall near the top of the container, but is operable to detect the vibration after it has propagated at least partially around the container wall and to generate a signal representative of the vibration at detection. The wireless communication device is coupled to the second transducer, and is operable to send a wireless signal representing the generated signal. The second wireless communication device is operable to receive the wireless signal, and the computer is coupled to the second wireless communication device. The computer is operable to determine if a signal representative of the vibration at detection has been received, determine a fluid mass in the container based on the time for the vibration to propagate at least partially around the wall from the first transducer to the second transducer, and to determine a fluid volume in the container based on the fluid mass. The computer is also operable to determine a fluid level in the container based on the fluid volume and to control the amplitude and frequency of the vibration introduced by the first transducer.

The details of one or more implementations of the invention are set forth in the accompanying drawings and the description below. Additionally, features of the various implementations will be apparent from the drawings and description, and from the claims.

DETAILED DESCRIPTION

Figure 1:
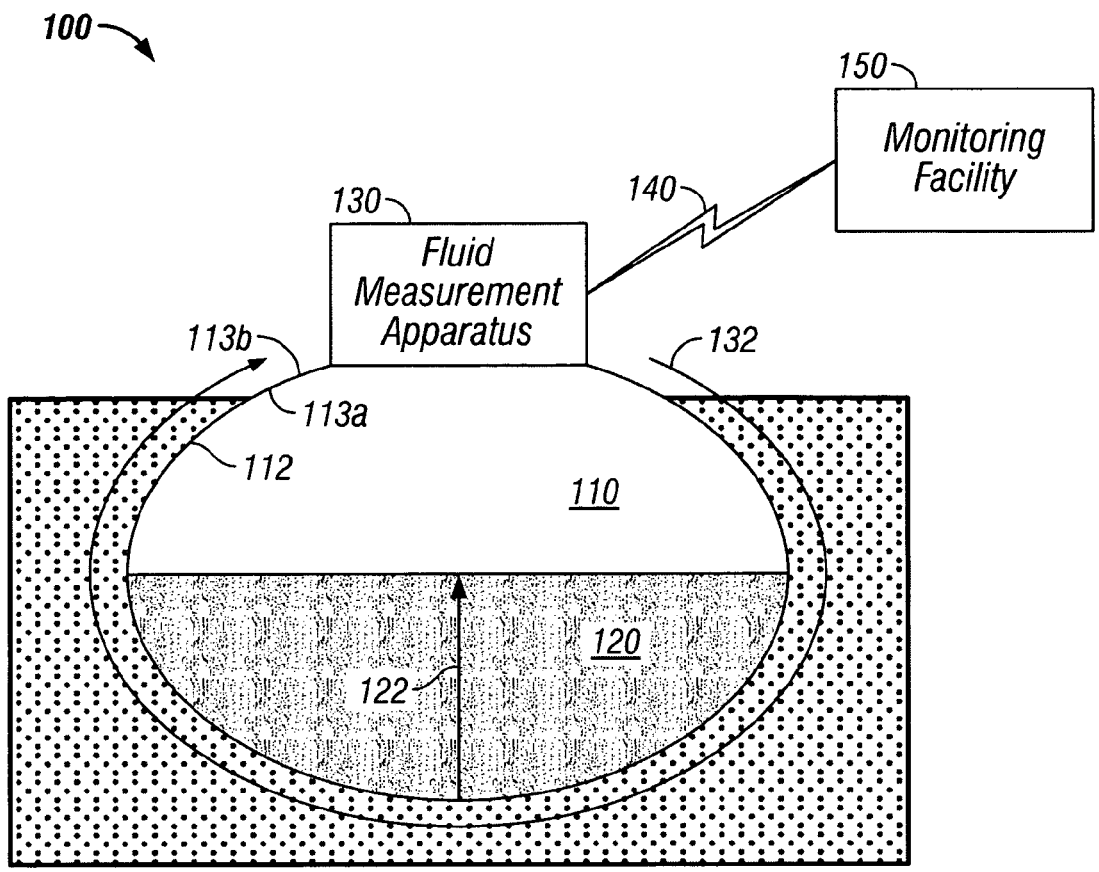
FIG. 1 is a diagram illustrating a system for fluid measurement.

FIG. 1 illustrates a system 100 for fluid measurement. As illustrated, system 100 includes a container 110 that holds a fluid 120 for which the level, represented by arrow 122, is to be measured, a fluid level being one example of a state of a fluid. System 100 also includes a fluid measurement apparatus 130 for performing the fluid level measurement and a wireless link 140 for sending information to a monitoring facility 150, which records and/or analyzes the fluid measurement. In general, fluid measurement apparatus 130 operates by introducing a vibration to a wall 112 of container 110 and detecting the vibration after it has propagated at least partially around the wall, the amount of fluid 120 affecting the propagation. The fluid level may be determined by fluid measurement apparatus 130 and/or monitoring facility 150.

In more detail, container 110 is an in-ground storage tank in the illustrated implementation. Wall 112 of container 110 has an inner surface 113a and an exterior surface 113b and is generally elliptical shape, although it may have any generally curved shape in other implementations. Wall 112 may be composed of metal, ceramic, composite, plastic, and/or any other appropriate material that will restrain a fluid and allow a vibration to propagate. In particular implementations, however, wall 112 is composed of steel. Furthermore, container 110 may have more than one wall and/or one or more end caps.

Fluid 120 may be a liquid, a gas, or a combination thereof. For example, fluid 120 may be gasoline, diesel, or liquid propane. Thus, fluid 120 may be flammable and/or explosive. Fluid 120 may also be a less dangerous liquid, like water or oil.

Fluid measurement apparatus 130 may be any appropriate system for introducing a vibration to wall 112 and detecting the vibration after it has propagated at least partially around wall 112, which may act as a waveguide for the introduced vibration. Introducing a vibration to wall 112 may include introducing a vibration onto the surface of the container, introducing a vibration into the wall, or otherwise establishing a vibration of the wall. The introduced vibration may be in any appropriate frequency regime. In particular implementations, however, the vibration is in the ultrasonic regime, and, in particular, between approximately 30 kHz and 150 kHz.

As illustrated, fluid measurement apparatus 130 may be coupled to exterior surface 113b near the top of container 110. In particular implementations, it may be beneficial to remove any exterior applications (e.g., paint) to exterior surface 113b before coupling apparatus 130 thereto.

Fluid measurement apparatus 130 detects the introduced vibration after it has propagated around wall 112 in the illustrated implementation. Typically, a vibration will take on the order of a few milliseconds to propagate around a container wall. The propagation time, however, may vary depending on the size of the container, the wall material, and the environmental conditions.

The fluid measurement apparatus generates a signal based on the detected vibration. The fluid measurement apparatus may also perform any appropriate conditioning (e.g., adding gain, providing analog-to-digital (A/D) conversion, or filtering) on the generated detection signal. To accomplish this, the fluid measurement apparatus may include a signal conditioning unit, an interface board, and/or any other appropriate device.

The fluid measurement apparatus may or may not determine level 122 of fluid 120 based on the properties of the introduced vibration at detection. If the fluid measurement apparatus does perform such a determination, the apparatus may include a computer for performing the determination.

Fluid measurement apparatus 130 is also operable to use wireless link 140 to wirelessly communicate information with monitoring facility 150. Wireless link 140 may be a radio frequency (RF) link, an infrared (IR) link, or any other appropriate wireless link for conveying information. Information may be sent, for example, by amplitude modulation, frequency modulation, phase modulation, or pulse modulation.

Monitoring facility 150 may be a data storage facility, a data processing facility, or a combination thereof. As such, it may include a computer for storing and/or processing the fluid level measurements and/or storing the fluid state, and related information. Monitoring facility 150 may also send commands to fluid measurement apparatus 130. For example, the monitoring facility may instruct the fluid measurement apparatus when to perform fluid level measurements.

In one mode of operation, fluid measurement apparatus 130 introduces a vibration to wall 112 of container 110. The vibration may be introduced at predetermined intervals, upon receipt of a command, or at any other appropriate time. The vibration propagates around wall 112 as one or more waves, such as a longitudinal wave, a shear wave, or a surface wave. The fluid measurement apparatus then waits to detect the vibration after it is has propagated at least partially around the container wall, a wave possibly entering fluid 120 at various points.

By examining the amplitude of the vibration at detection, the time for the vibration to propagate at least partially around the container wall, a combination of these, or any other appropriate criterion related to the vibration, monitoring facility 150 determines level 122, using a formula, a table look up, or other appropriate technique. For example, the amplitude and/or propagation time of a longitudinal wave may be used to determine level 122. As another example, the propagation time of a shear wave may be used to determine level 122. Note that the vibration may be introduced so that it does not propagate as a longitudinal wave.

The propagation of the vibration in wall 112 varies with the amount of fluid 120, affecting the amplitude and/or propagation time of the introduced vibration. Thus, comparing the characteristics of an introduced vibration in a tank with an unknown fluid level therein to the characteristics of an introduced vibration in a similar tank, or possibly even the same tank, with a known fluid level therein may provide an indication of the unknown fluid level.

If the container is being filled or drained when a measurement is desired, it may be possible to obtain a more accurate result after allowing the fluid to sit for several minutes. This should allow the fluid to stabilize and, hence, reduce entrapped air bubbles within the fluid, which may cause absorption and scattering, and result in reduced vibration amplitudes.

Fluid measurement apparatus 130 wirelessly sends a signal representing the generated detection signal to monitoring facility 150. Monitoring facility 150 determines the level, stores the determined level, and allows access thereto, for inventory control, billing, taxation, and/or other purposes.

System 100 has a variety of features. For example, because fluid measurement apparatus 130 may be coupled to the outside of container 110, fluid levels may be measured without having to access the interior of container 110. This allows apparatus 130 to be more readily installed and/or serviced. Furthermore, the system reduces the risk of contamination and/or explosion of fluid 120. As another example, because apparatus 130 may be located near the top of container 110, the apparatus may be installed more readily for in-ground tank applications. As an additional example, because fluid measurement apparatus 130 and monitoring facility 150 have wireless communication capabilities, fluid measurement apparatus 130 may be remote from monitoring facility 150. Furthermore, monitoring facility 150 may readily monitor a number of containers having a fluid measurement apparatus like fluid measurement apparatus 130.

Although FIG. 1 illustrates one implementation of a system for measuring fluid, other implementations may include fewer, additional, and/or a different arrangement of components. For example, a system may not include monitoring facility 150. Thus, the fluid measurement apparatus may determine and provide a local indication of fluid level, store the level for later retrieval, and/or perform further processing using the level, the results of which may be indicated and/or stored. Furthermore, although illustrated as being coupled to the top of container 110, the fluid measurement apparatus may be coupled to container 110 at any other appropriate location. Additionally, the fluid measurement apparatus may be coupled to the inside of the container. As another example, container 110 may be an above-ground storage tank, a truck tank, a railcar tank, or a barge tank. In general, therefore, container 110 may be any type of apparatus for restraining a fluid. As a further example, a system may not have a wireless link. Various wireline links (e.g., coaxial cables, optical fibers, or twisted-pair wires) may be used in these implementations.

In certain implementations, other fluid states may be determined, either in addition to or to the exclusion of the fluid level. A fluid state may, in general, be any measurable property and/or characteristic of a fluid. The state determinations may be performed by the fluid measurement apparatus, and stored locally and/or sent to the monitoring facility by the wireless link, or the determinations may be performed by the monitoring facility based on the fluid measurement.

For example, the mass of a fluid in the container may be determined, the amount of fluid in the container affecting the propagation of the vibration in the container wall. This may, for example, be accomplished by using a formula, a table look up, or any other appropriate technique.

As another example, the volume of a fluid in the container may be determined. This may, for example, be accomplished based on the mass of the fluid and the density of the fluid, by using a formula, by using a table look up, or by any other appropriate technique. In certain implementations, the volume may be adjusted for temperature, which may be measured by any appropriate temperature sensor.

Figure 2:
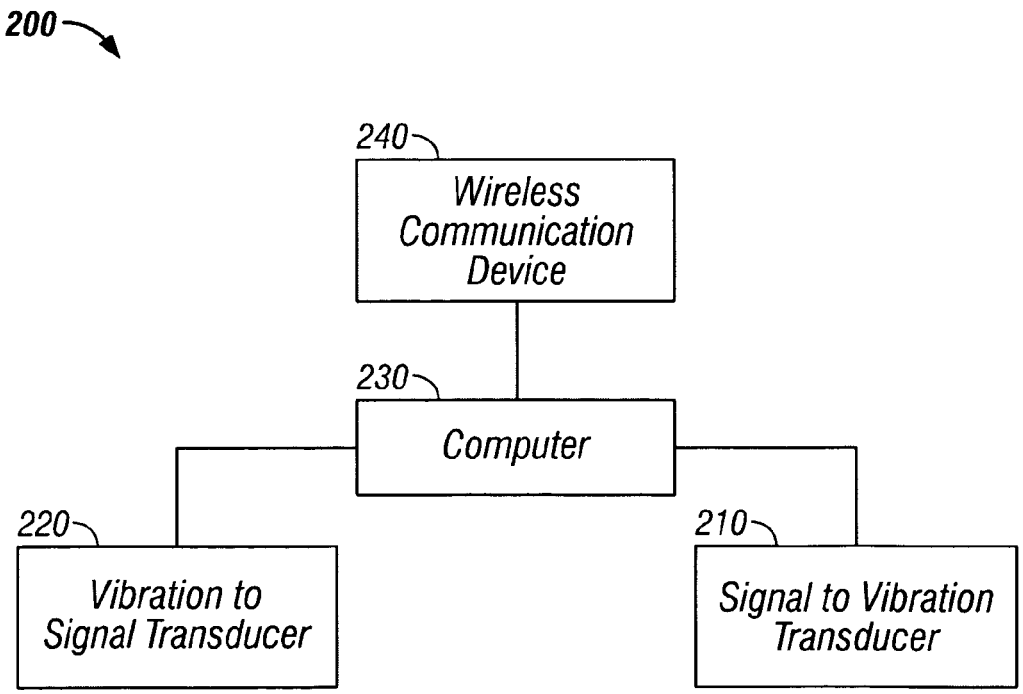
FIG. 2 is a block diagram illustrating an apparatus for fluid measurement.

FIG. 2 illustrates an apparatus 200 for fluid measurement. Apparatus 200 may be similar to fluid measurement apparatus 130 in FIG. 1

As illustrated, apparatus 200 includes a signal-to-vibration transducer 210, a vibration-to-signal transducer 220, a computer 230, and a wireless communication device 240. Signal-to-vibration transducer 210 is operable to generate a vibration in response to a command signal, and vibration-to-signal transducer 220 is operable to generate a signal in response to a detected vibration. Transducer 210 and transducer 220 are coupled to computer 230, which is operable to issue command signals to transducer 210 and receive generated signals from transducer 220. Computer 230 is also coupled to wireless communication device 240. Wireless communication device 240 is operable to send wireless signals representing information from computer 230 to a remote site, such as a monitoring facility.

In more detail, signal-to-vibration transducer 210 may be any appropriate device for generating a vibration in response to a command signal. The command signal may be in an analog or digital form, and may be included in a message. The generated vibration may be subsonic, audible, or ultrasonic. In particular implementations, however, the vibration is between approximately 30 kHz and 150 kHz. The frequency and/or amplitude of the vibration may be controllable. Examples of transducer 210 include an air transducer, a pulsed laser, and an impact device (e.g., a solenoid). The input amplitude of the introduced vibration is dependent, at least to some degree, on the specific transducer used, and directly affects the amplitude of the vibration at detection, but not the propagation time.

Vibration-to-signal transducer 220 may be any appropriate device for generating a signal in response to a detected vibration. The vibration may be subsonic, audible, or ultrasonic. In particular implementations, however, the vibration may be between approximately 30 kHz and 150 kHz. The generated signal may be in an analog or digital format, and may be part included in a message. In certain implementations, transducer 220 may be an air transducer. The sensitivity of the vibration detection is dependent, at least to some degree, on the configuration and receiving response of the transducer. In particular implementations, one or more amplifiers may be used to boost the introduction signal and/or the receive signal.

Computer 230 may be any appropriate device for processing information in a logical manner. For example, computer 230 may include an analog processor, a digital processor, or any other device for manipulating information in a logical manner. Computer 230 may also include a memory, such as, for example, random access memory (RAM), read-only memory (ROM), compact disk read-only memory (CD-ROM), and/or registers, for storing instructions and/or information. The instructions may, for example, dictate the operations of a digital processor.

Wireless communication device 240 may be any appropriate device for wirelessly sending information from computer 230 to a remote site. For example, wireless communication device may operate in the radio frequency (RF), the infrared (IR), or any other appropriate electromagnetic band for conveying information. Furthermore, the wireless communication device may use amplitude modulation, frequency modulation, phase modulation, pulse code modulation, or any other appropriate technique for encoding the information. In particular implementations, wireless communication device 240 may be a low power, spread spectrum wireless transceiver operating in the ISM band.

In one mode of operation, signal-to-vibration transducer 210 is coupled, possibly by a thin layer of hexagel or other appropriate acoustic coupling media, to the exterior of a container wall near the top of the container and is operable to introduce a vibration to the container wall such that the vibration propagates in the container wall as a shear wave. The vibration, however, may also propagate as other waves, such as a longitudinal wave and/or a surface wave, along with the shear wave. Thus, transducer 220 defines a point for detecting the introduced vibration.

The propagation of the vibration as one or more different types of waves may be dependent on the angle at which the vibration is introduced to the container wall. Typically, the angle of incidence for the transducer is between approximately 5° and 30°, and the critical angle at which a longitudinal wave becomes a surface wave is >approximately 25°; however, the latter angle may be quite dependent on the materials used. The introduction angle may, for example, be controlled by using different mountings for the transducer.

Vibration-to-signal transducer 220 is also coupled, by any appropriate acoustic coupling media, to the exterior of the container wall near the top of the container. Transducer 220 detects the vibration in the container wall, which will typically take on the order of a few milliseconds to propagate around a container wall. Based on the detection, transducer 220 generates a signal representative thereof for computer 230.

The spacing between transducer 210 and transducer 220 may be any appropriate value. In certain implementations, the spacing may range between approximately 0.25 inches and 5.0 inches. The spacing may, however, need to be tightly controlled for time of propagation measurements.

Computer 230 analyzes the signal from transducer 220 to determine a fluid state in the container. The determination may be based on the time for the introduced vibration to propagate around the container wall in the form of the shear wave, the amount of fluid affecting the propagation of the vibration in the container wall. Note that in some implementations, the propagation time may be for the shorter distance between the transducers. Wireless communication device 240 then sends a wireless signal representing the fluid state level to a remote site.

Although FIG. 2 illustrates one implementation of an apparatus for fluid measurement, other apparatuses for fluid measurement may have fewer, additional, and/or a different arrangement of components. For example, an apparatus may not have a wireless communication device. In these implementations, the apparatus may store the determined state for later retrieval. Also, other associated information may be stored. As another example, an apparatus may have an output device for presenting (visually, audibly, or otherwise) the determined state and/or other associated information. As an additional example, an apparatus may have devices for conditioning the generated signal. Examples of such devices include amplifiers, A/D Converters, and filters. Furthermore, devices for generating a waveform for the signal-to-vibration transducer may be included. As a further example, an apparatus may use one transducer for introducing and detecting a vibration. As another example, an apparatus may not have a computer.

Figure 3:
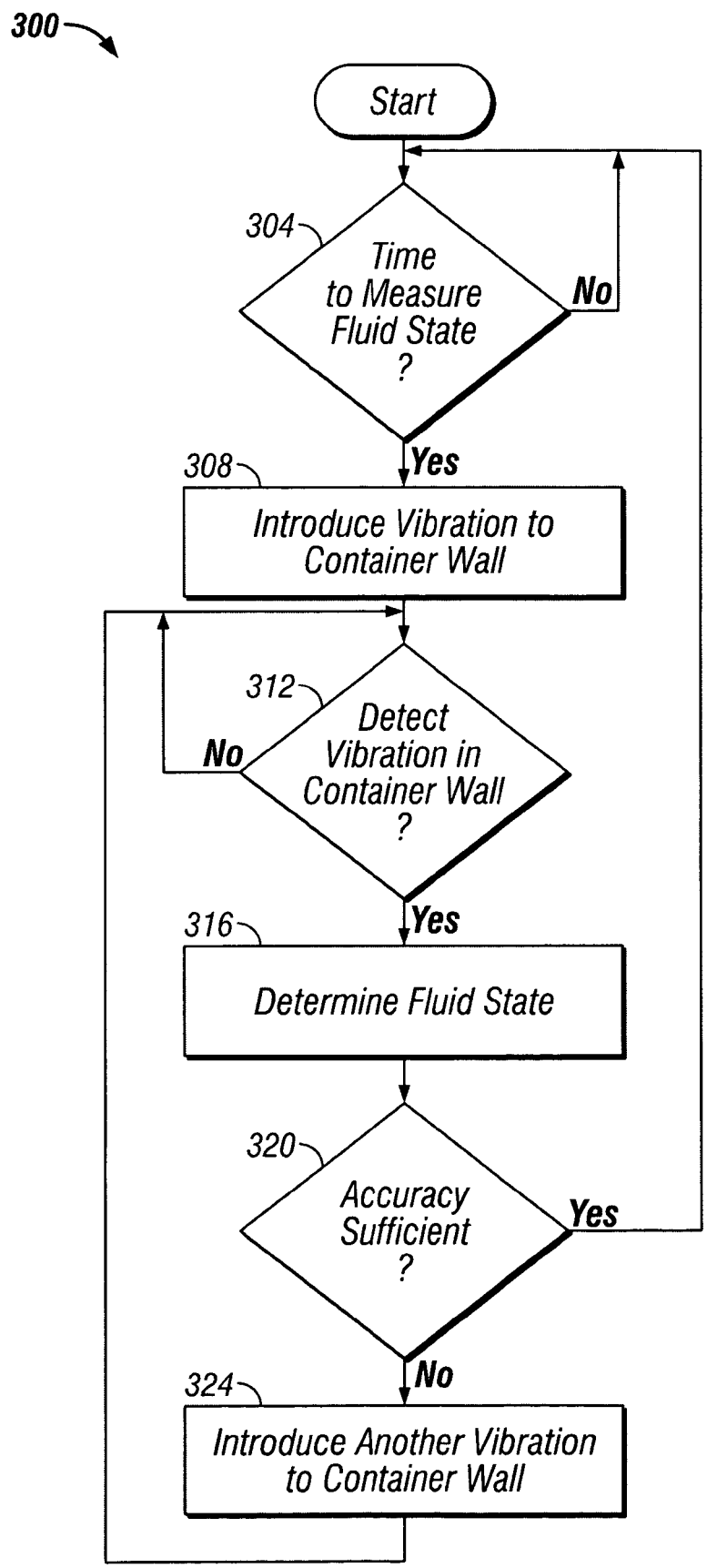
FIG. 3 is a flow chart illustrating a process for fluid measurement.

FIG. 3 illustrates a process 300 for fluid measurement. Process 300 may be implemented by an apparatus similar to apparatus 200, although other types of apparatuses or systems may also implement the process.

Process 300 begins with determining whether it is time to measure a state of a fluid (decision block 304). Determining whether it is time to measure a fluid state may be accomplished by determining whether a request for a fluid state measurement has been received, by determining that a designated period of time has expired, or by any other appropriate technique. A state of a fluid may, for example, be the fluid's mass, volume, level, pressure, and/or temperature.

If it is time to measure a fluid state, the process calls for introducing a vibration to a container wall (function block 308). The vibration may, for example, be introduced by a transducer mounted on the exterior of a container wall near the top of the container. The vibration may propagate in the wall as a longitudinal wave, a shear wave, or a combination thereof. In particular implementations, however, a shear wave is propagated without a longitudinal wave. Other vibrations may also be excited in, on, or near the wall.

The process continues with waiting to detect a vibration in the container wall (decision block 312). Typically, a vibration will take on the order of a few milliseconds to propagate around a container wall. The propagation time, however, may vary depending on the size of the container, the wall properties, and the environment. Also, some waves (e.g., a longitudinal wave) may propagate partially through the fluid in the container, which may also vary the propagation time. The detection may be made by any appropriate type of vibration detector, and a signal may be generated based on the detection.

Once the vibration is detected, the process continues with determining a fluid state (function block 316). The determination may be made based on the amplitude of the vibration at detection, the time for the vibration to propagate around the container wall, a combination of these, or upon any other appropriate criterion related to the vibration. In particular implementations, the vibration is converted to a signal upon detection, and this signal is analyzed to determine the fluid state.

The process continues with determining whether the accuracy of the fluid state measurement is sufficient (decision block 320). Determining whether the accuracy of the fluid state measurement is sufficient may be accomplished by determining that a predefined number of measurements are required for accuracy, by determining that detected properties of the previously introduced vibration are suspect (e.g., amplitude and/or propagation time have unexpected values or do not correlate), or by any other appropriate technique. If the accuracy is not sufficient, the process calls for introducing another vibration to the container wall (function block 324). The new vibration may be the same as the previous vibration or different from the previous vibration, in amplitude, frequency, or any other appropriate property.

The process then calls for waiting to detect the vibration (decision block 312), determining the fluid state (function block 316), and determining whether the accuracy is sufficient (decision block 320). The accuracy may be determined using the current measurement, the previous measurement, or a combination thereof. The process may continue cycling through blocks 312–324 for any number of times.

Once the accuracy of the determined fluid state is sufficient, however, the process calls for again determining whether it is time to make a fluid state measurement (decision block 304).

Although FIG. 3 illustrates a process for fluid measurement, other processes for fluid measurement may have fewer, additional, and/or a different arrangement of operations. For example, a process may not call for determining whether it is time to perform a fluid state measurement. This may occur, for example, if a process is to continuously make such measurements or if a process makes a measurement when power for making the measurement is supplied. As another example, a process may call for introducing another vibration if a vibration is not detected within a predefined period of time. As a further example, a process may call for introducing a predefined number of vibrations before determining the fluid state. As an additional example, a process may not call for determining whether the accuracy is sufficient. As a further example, a process may call for controlling the introduction of the vibration, based on amplitude, frequency, or any other appropriate property. As another example, a process may call for storing the determined fluid state and/or sending a wireless signal representing the fluid state. As an additional example, a process may call for sending a wireless signal representing the detected vibration.

The techniques discussed herein may have applicability in a variety of fields other than measuring fluids in containers. For example, the techniques may be useful for measuring a state of a fluid in structures other than containers (e.g., pipes). As another example, the techniques may be useful for measuring a state of substances other than fluids in containers (e.g., corn, dirt, wood, or rocks).

A variety of implementations have been described, and numerous other implementations have been mentioned. Furthermore, a variety of additions, subtractions, substitutions, and/or modifications may be made to the described and mentioned implementations while still achieving fluid measurement. It is intended, therefore, that the scope of the invention be measured by the following claims.

What is claimed is:

1. A system for measuring fluid in a container, the system comprising:
   one or more transducers operable to:
      introduce a vibration to a container wall,
      detect an introduced vibration that has propagated at least partially around a container wall in more than one vertical propagation direction, and
      generate a signal representative of a detected vibration; and
   a computer operable to determine a state of a fluid in a container based on a signal representing an introduced vibration that has propagated at least partially around a container wall in more than one vertical propagation direction;
wherein the one or more transducers comprises at least one air transducer operable to introduce a vibration to a container wall.

2. A system for measuring fluid in a container, the system comprising:
a container for holding a fluid, the container comprising a wall having an inner surface and an exterior surface;
a first transducer coupled to the exterior surface of the container wall near the top of the container, the first transducer operable to introduce a vibration to the container wall;
a second transducer coupled to the exterior surface of the container wall near the top of the container, the second transducer operable to detect the vibration after it has propagated at least partially around the container wall and to generate a signal representative of the vibration at detection;
a wireless communication device coupled to the second transducer, the wireless communication device operable to send a wireless signal representing the generated signal; and
a second wireless communication device, the second wireless communication device operable to receive the wireless signal;
a computer coupled to the second wireless communication device, the computer operable to:
determine if a signal representative of the vibration at detection has been received;
determine a fluid mass in the container based on the time for the vibration to propagate at least partially around the wall from the first transducer to the second transducer,
determine a fluid volume based on the fluid mass,
determine a fluid level based on the fluid volume, and
control the amplitude and frequency of the vibration introduced by the first transducer.

3. A system for measuring fluid in a container, the system comprising:
one or more transducers operable to:
introduce a vibration to a container wall,
detect an introduced vibration that has propagated at least partially around a container wall in more than one vertical propagation direction, and
generate a signal representative of a detected vibration; and
a computer operable to determine a state of a fluid in a container based on a signal representing an introduced vibration that has propagated at least partially around a container wall in more than one vertical propagation direction,
wherein the one or more transducers are further operable to detect an introduced vibration that has propagated at least a majority of the way around a circumference of a container wall in more than one vertical propagation direction; and
the computer is further operable to determine a state of a fluid in a container based on a signal representing an introduced vibration that has propagated at least a majority of the way around a circumference of a container wall in more than one vertical propagation direction.

4. A method for measuring fluid in a container, the method comprising:
introducing a vibration to a container wall;
detecting the vibration in the container wall after the vibration has propagated at least partially around the container wall in more than one vertical propagation direction; and
determining a state of a fluid in the container based on the detection of the vibration,
wherein detecting the vibration in the container wall after the vibration has propagated at least partially around the container wall in more than one vertical propagation direction comprises detecting the vibration after it has propagated at least a majority of the way around a circumference of the container wall.

5. A system for measuring fluid in a container, the system comprising:
means for introducing a vibration to a container wall;
means for detecting an introduced vibration that has propagated at least partially around a container wall in more than one vertical propagation direction and for generating a signal representing a vibration at detection; and
means for determining a state of a fluid in a container based on a signal representing an introduced vibration that has propagated at least partially around the container wall,
wherein the means for detecting an introduced vibration that has propagated at least partially around a container wall in more than one vertical propagation direction and for generating a signal representing a vibration at detection is further operable to detect an introduced vibration that has propagated at least a majority of the way around a circumference of a container wall in more than one vertical propagation direction; and
the means for determining a state of a fluid in a container based on a signal representing an introduced vibration that has propagated at least partially around a container wall is further operable to determine a state of a fluid in a container based on a signal representing an introduced vibration that has propagated at least a majority of the way around a circumference of a container wall in more than one vertical propagation direction.

6. A method for measuring fluid in a container, the method comprising:
receiving a signal representing a vibration detected after being introduced to and propagating at least partially around a container wall in more than one vertical propagation direction; and
determining a state of a fluid based on the signal,
wherein receiving a signal representing a vibration detected after being introduced to and propagating at least partially around a container wall in more than one vertical propagation direction comprises receiving a signal representing a vibration detected after being introduced to and propagating at least a majority of the way around a circumference of a container wall in more than one vertical propagation direction.

7. A system for measuring fluid in a container, the system comprising:
a computer operable to:
determine whether a signal representing a vibration detected after being introduced to and propagating at least partially around a container wall in more than one vertical propagation direction has been received, and
determine a state of a fluid based on the signal,
wherein the computer is further operable to determine a state of a fluid in a container based on a signal representing a vibration detected after being introduced to and propagating at least a majority of the way around a circumference of a container wall in more than one vertical propagation direction.

8. An article comprising a machine-readable medium storing instructions operable to cause one or more machines to perform operations comprising:

determining whether a signal representing a vibration detected after being introduced to and propagating at least partially around a container wall in more than one vertical propagation direction has been received; and determining a state of a fluid based on the signal, wherein determining a state of a fluid based on the signal comprises determining a state of a fluid in a container based on a signal representing a vibration detected after being introduced to and propagating at least a majority of the way around a circumference of a container wall in more than one vertical propagation direction.

* * * * *